United States Patent [19]

Bottomley

[11] 4,049,798
[45] Sept. 20, 1977

[54] METHOD FOR THE TREATMENT OF HERPES SIMPLEX

[75] Inventor: William K. Bottomley, Potomac, Md.

[73] Assignees: William K. Bottomley, Potomac, Md.; O. J. Brightwell, Sacramento, Calif.; Thomas J. Newell, III, Bethesda, Md.

[21] Appl. No.: 656,742

[22] Filed: Feb. 9, 1976

Related U.S. Application Data

[63] Continuation of Ser. No. 531,459, Dec. 11, 1974, abandoned.

[51] Int. Cl.$^2$ .................... A61K 35/78; A61K 31/365
[52] U.S. Cl. ...................................... 424/195; 424/280
[58] Field of Search .......................................... 424/280

[56] References Cited

U.S. PATENT DOCUMENTS 2,888,381  5/1959  Freedman et al. .................... 424/280
3,132,154  5/1964  Meyer-Doring ...................... 424/280

OTHER PUBLICATIONS

Holden et al., *Chemical Abstracts* 31:1870$^2$ (1936).
Stone, *The Healing Factor*, Gosset & Dunlap Publishers, (1972), pp. 74–75.
Holden et al., *Chemical Abstracts* 32:233$^5$ (1937).
*Physicians Desk Reference*, (1971), p. 1372.

*Primary Examiner*—Norman A. Drezin
*Attorney, Agent, or Firm*—Bacon & Thomas

[57] ABSTRACT

A method for the treatment of Herpes Simplex comprising administration of a mixture comprising (a) Vitamin C and (b) Vitamin P.

7 Claims, No Drawings

METHOD FOR THE TREATMENT OF HERPES SIMPLEX

This is a continuation of application Ser. No. 531,459, filed Dec. 11, 1974 now abandoned.

BACKGROUND OF THE INVENTION

1. Field of the Invention

This invention relates to a method for treatment of Herpes Simplex and more particularly to a method for the treatment of Herpes Simplex by administration of a mixture of L-ascorbic acid (Vitamin C) and bioflavonoids (Vitamin P).

2. Description of the Prior Art

One of the more common ailments which affects man is known as the simple Herpes of the lips, otherwise known as Herpes Simplex, commonly called cold sores. To the present time and to Applicant's knowledge there is no remedy available for a rapid cure of simple Herpes Simplex or cold sores, although there are various preparations therefor on the commercial market. The present invention provides a composition and method for use which is effective for the treatment of Herpes Simplex.

Next to the common cold there is probably no more common ailment than simple Herpes of the lips. Initial infection usually occurs in childhood. Mild trauma such as that associated with dental treatment, abrasion of the oral mucosa, or any disease which produces a fever or an increased metabolic rate may serve as a predisposing factor. Herpetic lesions frequently accompany nutritional deficiencies, allergy to certain foods, or nervous or emotional states. There are many people who with every cold develop a blister or two on the lips, which soon break down to give a sore encrusted patch that usually heals completely in 10 to 14 days. Some particularly sensitive individuals can expect a crop or blisters with every exposure to a cold wind or an undue amount of sunshine. Anyone who suffers from Herpes can expect to continue having attacks, usually on the same area of the skin or the lips and provoked by the same sort of circumstances, for the rest of his life. Simple Herpes of the lips is generally considered to be caused by a virus.

It might be easy to convince the fishermen, hunters, and sunworshippers to accept their occasional vesicle on the lip as an incident of minor importance. However, there are others whose periodic encounter with this virus is so extreme that they would challenge the nomenclature "Simplex." Some of the more clinically dramatic manifestations of this virus are: Involvement of the mucous membrane of the nose accompanied by secondary infection; secondary outbreak in the genital region; primary vesicle formation of the zygomatic prominence spreading into the eye resulting in scarring of the cornea; periodic organic psychosis associated with recurrent *Herpes labialis;* primary outbreak on the ear lobe with spreading into the auditory canal; generalized cutaneous Herpes Simplex; and *Herpes Gestationis,* a dermatitis Herpetiformis affecting the female during the second and third trimesters of pregnancy.

In contradistinction to other viral diseases, there is no permanent immunity after an initial Herpes Simplex virus infection. The treatment is aimed at palliation. Various topical remedies used for the treatment of *Herpes Labialis* include the application of silver nitrate, alum styptic pencil, calamine lotion, camphor, phenol, alcohol, tincture of benzoin and zinc chloride. These substances coagulate and numb the superficial exposed nerve endings providing symptomatic relief but do not alter the course of these lesions to any measureable extent. Furthermore, continuous use of the more severe caustics not only delays healing but may promote fibrous rather than epithelial resolution.

More recently suggested topical therapeutics for use in this area are: 5% aureomycin ointment, which reduced the duration of the lesion to an average of 6.1 days, with proportionally better results with early institution of therapy; and application of triamicinolone acetonide in orabase twice a day, which promoted healing and diminished the time of painful symptoms. When applied during the prodromal stage it prevented vesicle formation in some cases.

Although no form of systemic therapy has been consistently successful in preventing recurrent episodes of Herpes Simplex, various systemic therapeutics reportedly are of value in diminishing the clinical manifestations. Thus, there has been reported the successful treatment of Herpes Gestationis (*Dermatitis Herpetiformis*) with 0.5 gram of sulfa-thiazole twice daily. However, prolonged treatment with this drug is hazardous, and the symptoms are likely to recurr if the medication is withdrawn or dosage is reduced. It has also been found that serial vaccinations with smallpox vaccine given every 2 weeks for 16 weeks resulted in attenuated outbreaks in 67% of the 54 patients treated. In a control group receiving inactivated smallpox vaccine, 52% were similarly affected. Another clinical experience with smallpox vaccine therapy showed relief from future outbreaks for 2 to 12 years in 88% of 100 cases. It has also been reported that intramuscular injections of 5 cc. of gamma globulin administered on consecutive days apparently reduced the symptomatic period and the time of healing of the labial lesions. Daily intramuscular injections of 1.3 ml. of protamide, a processed and denatured proteolytic enzyme, was the therapy used by one researcher. The pain was generally relieved within 1 or 2 hours following the initial injection and the lesions began to dry up after the second injection. No side effects were seen in the 12 cases treated. An ointment of 0.5% of Neo-Cortef was applied locally at the same time. These patients were treated in the vesicle stage with no statement as to the length of time it had been present. There is always the possibility of an anaphalactoid reaction with this drug however.

In two instances of vaccination using unmodified material taken from the sites of recurrent Herpes Simplex infections, a second site of recurrent Herpes Simplex was initiated. However, it has been reported that the vaccination of mice with ultraviolet attenuated Herpes Simplex virus suspension has produced levels of Herpes Simplex antibodies sufficient to withstand challenging doses of live Herpes Simplex viruses.

L-ascorbic acid is well known in the art, is generally designated as Vitamin C and is considered to be one of the vitamins necessary to human health. Mixtures of citrus bio-flavonoids are known in the art as Vitamin P and both of these materials have been used in various therapeutic areas. In fact, both of these materials are available on the commercial market for use in known areas. They have also been used in admixture. Thus, British Pat. No. 674,909 and U.S. Pat. No. 2,888,381 disclose combinations of an aqueous solution of Vitamin P and Vitamin C for use in the preservation and repair of teeth. Further, U.S. Pat. No. 2,888,381 discloses use of solutions of citrus bio-flavonoids and ascorbic acid in therapeutic compositions containing propylene glycol which therapeutic compositions are said to be useful because of their effect on capillary fragility. U.S. Pat. No. 2,888,381 indicates that the complex of the citrus bio-flavonoids, known as Vitamin P, with ascorbic acid added, has been sold by the U.S. Vitamin Corporation in the United States under the tradename C.V.P. since prior to 1950. In addition, the literature reference, "Facts and Comparisons", 4th Edition, 1963, page 159 (Flavanoids), indicates that Duo C.V.P. is a 50—50 mixture of citrus bio-flavonoid compounds (Vitamin P) and ascorbic acid (Vitamin C). This article points out that this mixture or complex is useful in the formation of intercellular cement thus thickening the capillary wall and increasing its efficiency as a biological filter and also as being valuable in other areas. However, use in the treatment of Herpes Simplex is not mentioned. U.S. Pat. No. 3,132,154 also discloses that ascorbic acid is known to have bactericidal effects and that it is readily destroyed or oxidized to an ineffective compound in an infected body or inflamed tissue.

In none of the above-discussed prior art references or in any other reference of which Applicant is aware is there disclosed a suggestion for the use of a mixture of ascorbic acid and citrus flavonoids for the treatment of Herpes Simplex. Therefore, the present invention is considered to provide a significant advance in this area in the unexpected discovery that a mixture of Vitamin C and Vitamin P is useful in the treatment of Herpes Simplex.

SUMMARY OF THE INVENTION

It is accordingly one object of this invention to provide a method for the treatment of Herpes Simplex.

It is a further object of this invention to provide a composition suitable for the treatment of Herpes Simplex or cold sores which is safe, effective and rapid in action.

A still further object of the invention is to provide a method for the treatment of Herpes Simplex by the administration to the patient of a mixture comprising ascorbic acid (Vitamin C) and a citrus bio-flavonoid (Vitamin P).

Other objects and advantages of the present invention will become apparent as the description thereof proceeds.

In satisfaction of the foregoing objects and advantages there is provided by this invention a method for the treatment of Herpes Simplex which comprises administering to a patient suffering therefrom a therapeutically effective amount of a mixture of L-ascorbic acid and citrus bio-flavonoids.

DESCRIPTION OF PREFERRED EMBODIMENTS

According to this invention there is provided a method for the treatment of Herpes Simplex or cold sores, which method comprises administering to the patient a mixture comprising L-ascorbic acid and citrus bio-flavonoids. As pointed out above, the ascorbic acid is a well known compound and is known in the art as Vitamin C. This material has been deemed to be an important factor in animal and human health including the health of oral tissues. As indicated above, the citrus bio-flavonoids are also well known as Vitamin P. While both the Vitamin C and Vitamin P are known to be independently useful as valuable therapeutic materials, and mixtures of these materials are also known to be therapeutically useful, it was nevertheless unexpected to discover that this mixture is effective in the treatment of Herpes Simplex or for the treatment of cold sores. In the treatment it appears that the combination of components provides a synergistic effect not realized by either of the components alone.

The most characteristic quality of Herpes Simplex, irrespective of the severity of its manifestations, is its tendency to recur. Thus, the art now recognizes that at the time of the primary infection, some of the surface cells of the skin of the lips, may be involved without being destroyed. In some manner these cells become tolerant of, or resistant to, the virus. These skin cells and their descendents remain infected, but for the most part give no evidence of the action of the virus. However, in the areas of the lip that are infected with Herpes Virus, it is assumed that in the basal cell layer, the virus is multiplying at almost exactly the same rate as the cells themselves multiply. While there is an antibody in the blood which can prevent passage of the virus to distant cells, the blood serum and its antibody can make no contact with the interior of a cell, since if a virus is actually inside a cell it cannot be influenced by antibody circulating in the blood.

The Herpes virus then is existing in these cells in a delicate state of equilibrium and its rate of growth has adjusted to that of the cell. With a relatively minor change, e.g. in the body temperature, this equilibrium is disturbed and the virus takes control. Multiplication of the virus occurs, the cells are damaged, break down and inflammatory changes appear. The virus is liberated and probably the mild, circumscribed character of most Herpes lesions is due to the fact that any spread of infection by liberated virus is stopped by the antibody that is already in the blood. Therefore, the paradoxical situation exists where there is antibody in the blood to the virus but recurrent lesions continue to appear due to the action of the virus.

If one can accept the theory that the Herpes virus is located intracellularly and thereby safe from the circulating antibody, it appears logical that any efforts to control or destroy this virus by vaccines would be futile. Thus, perhaps the logical stage to attack the clinical manifestation of this virus would be in the initial phase of inflammation, or prodromal stage, in an attempt to reinforce the cellular resistance to the virus and restore the state of equilibrium.

Nevertheless, successful treatments appear to be symptomatic rather than curative. A question may be logically raised as to the possibility that many of the cases diagnosed as Herpes Simplex are actually Herpes-like manifestations. This would be analogous to allergic symptoms being diagnosed as a cold. In view of the difficulties incident to this problem it was discovered that a treatment directed toward relieving the symptoms of Herpes irrespective of the cause would be successful. The present invention thus provides a composition useful for this purpose.

In the treatment of the clinical manifestations of a Herpes Simplex-like syndrome, the criteria of an ideal therapeutic from the standpoint of the patient would be:
1. Effectiveness
   A. Abort lesion if used in prodromal stage or shorten duration of lesion
   B. Abort any secondary manifestations
2. Safe (i.e., no harmful side effects)
3. Easily administered
4. Should have a constant effect
5. Inexpensive 6. Easily obtainable (i.e., without prescription)

The composition of the present invention meets these criteria in providing a safe and effective treatment for Herpes Simplex.

According to this invention, optimum results were obtained by starting treatment as soon as possible after the patient recognized the first symptom of an apparent Herpes attack. In the cases where therapy began with the first recognizable prodrome, the vesicle stage was completely aborted. The treatment is proportionally less effective with the time lapse between the origin of the Herpes attack and the beginning of the treatment. After the Herpes Simplex has reached the blister stage, the administration of the ascorbic acid and bio-flavonoids composition appears to reduce both the period of tenderness and the time of healing.

The products of this invention are especially suitable for oral administration in the conventional manner, that is, by the formation of capsules or pills and administration to the patient orally. However, administration by injection may also be carried out using any of the well known carriers and adjuvants therefor as is well known in the art. The dosage amount of the mixture of the invention will comprise a minimum of about 0.70 mg./kg. of body weight based on its Vitamin P content. Having in mind the lack of toxicity of both of the ingredients of the mixture, there is no real maximum dosage for the mixture and truly massive doses will be effective. There is, however, reached a point of diminishing returns and dosage of about 1.5 mg./kg. is preferred.

The essential components of the invention may be administered as a mixture comprising only these components or they can be compounded with suitable adjuvants or carriers of the type known to the art. Also, there may be included other materials which provide additional advantages such as other vitamins and the like.

The preferred composition for administration according to this invention includes a mixture comprising about 50 weight percent of the ascorbic acid and about 50 weight percent of the citrus bio-flavonoid complex. However, the percent of each component may be varied so that there may be present about 20–50 weight percent of the ascorbic acid and about 80–50 weight percent of the bio-flavonoid complex.

One dosage actually orally administered in the use of the preferred composition was one 200 mg. capsule containing Vitamin C and Vitamin P in equal amounts by weight at once followed by one capsule 3 times a day until complete remission occurs which will usually be within 2 to 4 days. Larger capsules (400 mg.) and more frequent, 4 times a day, doses did not appear to result in a speedier remission of the disease.

The following examples are presented to illustrate the invention but it is not to be considered as limited thereto. In these examples and throughout the specification parts are by weight unless otherwise indicated.

The general method for use of the compositions of this invention comprises that of clinical observations on patients seen in routine dental practice. These patients had a history of periodic outbreak of "cold sores" or "fever blisters". There were no limitations made regarding age, sex or complexion. Since there is some controversy as to whether the extraoral and intraoral lesions are both caused by the Herpes virus, only extraoral lesions were treated. No attempts were made to identify the virus or carry out any diagnostic procedures other than by simple observation and recording of the clinical appearance of the lesion and history prior to onset. Treatment consisted of administering a 200 mg. (or 400 mg.) capsule containing equal amounts of ascorbic acid and citrus bio-flavonoids by weight at once followed by one capsule 3 times a day. No local treatment was employed. Patients were re-examined every 24 hours for pain and appearance of the affected area. Complete remission was judged by disappearance of all signs and symptoms associated with a Herpes Simplex Syndrome; i.e., the affected area was not painful, itching, red swollen or different from the adjacent skin in appearance. The following case histories represent the responses obtained by the therapy employed.

EXAMPLE 1

A white male, age 22, red hair, fair complexion, skin very sensitive to sunlight, history of blisters on lips after prolonged exposure to sunlight.

Examination: small, tender area on vermilion border of lower lip which the patient, from past experience, complained would develop into a blister.

Treatment: One capsule of an equal mixture of Vitamin C and Vitamin P (200 mg.) at once followed by one capsule 3 times a day. No local treatment was employed.

24 hours later there was no increase in size of the tender area.

In 48 hours the pain was alleviated.

In 72 hours there was complete remission. There was no vesicle formation.

EXAMPLE 2

A white male, age 32, dark complexion, history of blisters on lower lip after prolonged exposure to sunlight.

Examination: small, tender area on vermilion border of lower lip. The patient stated that this particular area was where he always developed a "cold sore" or "fever blister" and no other area was affected.

Treatment: One 200 mg. capsule containing equal amounts of weight of Vitamin C and Vitamin P at once followed by one capsule 3 times a day. No local treatment was employed.

24 Hours later there was decreased pain in the area with no increase in size.

In 48 hours the area was no longer painful. The affected area was somewhat more firm to palpation than the surrounding tissue.

In 72 hours there was complete remission. There was no vesicle formation.

EXAMPLE 3

A white male, age 27, brown hair, medium complexion, history of blisters after prolonged exposure to sunlight.

Examination: Blisters on lower and upper lips extending to the base of the nares (the onset had occurred two days before).

Treatment: One 400 mg. capsule containing equal amounts of Vitamin C and Vitamin P at once followed by one capsule 3 times a day. No local treatment was employed.

24 Hours later there was no noticable change.

48 Hours later the blistered areas had crusted over with decreased tenderness in the area.

In 72 hours the area was no longer tender and had decreased in size.

In 96 hours the affected areas were still distinguishable as non-elevated, red areas.

In 5 days there was complete remission.

The patient was instructed to return at the first symptom of another Herpes attack which he subsequently did a few weeks later. His treatment then was one Vitamin C and Vitamin P capsule (200 mg.) at once followed by one capsule 3 times a day. No local treatment was employed.

In 24 hours the pain was gone.

In 48 hours there was complete remission. There was no vesicle formation.

EXAMPLE 4

A white male, age 40, dark complexion, history of "cold sores". The patient's chief concern was that, from past experience, in approximately 48 hours after the primary lesion on the lip, there would be similar manifestations in the genital region.

Examination: Numerous small blisters in a cluster extending from the vermilion border of the upper lip to the base of the nares. These had been present when the patient awoke 3 hours previously.

Treatment: One 400 mg. Vitamin C and Vitamin P capsule (200 mg. of each) at once followed by one capsule 3 times a day. No local treatment was employed.

24 Hours later no blisters were present. One small, red, slightly elevated area remained on the vermilion border, which was tender.

48 Hours later all pain was gone. A small, red, slightly elevated area was still distinguishable on the vermilion border.

72 Hours later, the red area had been cut by the patient while shaving and now was crusted over. The Vitamin capsules were discontinued.

Five days later there were no signs or symptoms present, and the patient never experienced the secondary outbreak in the genital region.

The results obtained from the treatment of 19 cases including Examples 1–4, and the summary of these results are shown in Table I and Table II, respectively.

TABLE I

Results of Treatment of 19 Cases of Herpes Simplex-Like Syndrome

| Case No. | Before Treatment | After Treatment Pain | After Treatment Other | Total | Vesicle Formation |
|---|---|---|---|---|---|
| 1 | 2 | 2 | 5 | 7 | + |
| 2 | 0 | 2 | 3 | 3 | − |
| 3 | 0 | 1 | 3 | 3 | − |
| 4 | 0 | 2 | 4 | 4 | − |
| 5 | 2 | 3 | 5 | 7 | + |
| 6 | 0 | 1 | 2 | 2 | − |
| 7 | 0 | 2 | 4 | 4 | − |
| 8 | 1 | 2 | 4 | 4 | − |
| 9 | 0 | 2 | 4 | 4 | − |
| 10 | 1 | 2 | 5 | 5 | − |
| 11 | 2 | 2 | 4 | 6 | + |
| 12 | 0 | 1 | 3 | 3 | − |
| 13 | 0 | 1 | 3 | 3 | − |
| 14 | 1 | 2 | 5 | 6 | + |
| 15 | 0 | 2 | N.O. |  | − |
| 16 | 0 | 1 | 2 | 2 | − |
| 17 | 0 | 1 | 3 | 3 | − |
| 18 | 0 | 1 | 2 | 2 | − |
| 19 | 2 | 2 | 5 | 7 | + |

TABLE II

Summary of Results of 19 Cases of Herpes Simplex-Like Syndrome

| No. of Cases | Before Treatment | After Treatment Pain | After Treatment Other | Total | Vesicle Formation (Percent of Cases) |
|---|---|---|---|---|---|
| 12 | 0 | 1.4 | 3.0 | 3.0 | 0 |
| 3 | 1 | 2.0 | 4.7 | 5.7 | 33 |
| 4 | 2 | 2.2 | 4.7 | 6.7 | 100 |
| 19 | 0.56 | 1.6 | 3.6 | 3.8 | 26 |

In the above tables, the effectiveness of the ascorbic acid + bio-flavonoids in dosages of 600–1200 mg. per day was evaluated in the treatment of 19 cases of a Herpes-like snydrome. As the tables indicate, complete remission of symptoms was obtained in 2 to 4 days in all cases where treatment was started when premonitory symptoms were recognized. Complete remission of symptoms was obtained in a maximum of 7 days, when treatment was initiated two days after recognition of the syndrome.

The invention has been described herein with reference to certain preferred embodiments, however, the invention is not to be considered as limited thereto as obvious variations thereon will become apparent to those skilled in the art.

What is claimed is:

1. A method for the treatment of recurrent herpes simplex labialis which comprises administering to a patient suffering therefrom a therapeutically effective amount of a mixture comprising (a) about 50 weight percent L-ascorbic acid and (b) about 50 weight percent citrus bio-flavonoids.

2. A method according to claim 1 wherein at least about .70 mg./kg. of body weight of said mixture based on its citrus bio-flavonoids content is administered to the patient.

3. A method according to claim 2 wherein about 1.5 mg./kg. is administered.

4. A method according to claim 2 wherein the mixture is in the form of a pill and administration is orally.

5. A method according to claim 2 wherein the mixture is in the form of a capsule and administration is orally.

6. A method according to claim 1 wherein treatment is carried out by oral administration of the mixture in equal amounts over a period of two to four days.

7. A method according to claim 1 wherein said mixture contains 200 mg. to 400 mg. of equal parts of L-ascorbic acid and citrus bio-flavonoids.

* * * * *